(12) United States Patent
Huth

(10) Patent No.: US 6,468,469 B2
(45) Date of Patent: Oct. 22, 2002

(54) REUSE DETERMINATION FOR HIGH LEVEL DISINFECTANT

(75) Inventor: Stanley W. Huth, Newport Beach, CA (US)

(73) Assignee: Metrex Research Corporation, Orange, CA (US)

( * ) Notice: Subject to any disclaimer, the term of this patent is extended or adjusted under 35 U.S.C. 154(b) by 0 days.

(21) Appl. No.: 09/812,088

(22) Filed: Mar. 19, 2001

(65) Prior Publication Data

US 2002/0131890 A1 Sep. 19, 2002

Related U.S. Application Data

(60) Provisional application No. 60/235,727, filed on Sep. 27, 2000.

(51) Int. Cl.⁷ .............................................. G01N 33/48
(52) U.S. Cl. ................................ 422/3; 422/28; 422/31
(58) Field of Search ............................... 422/3, 28, 31, 422/61, 58; 73/53.01

(56) References Cited

U.S. PATENT DOCUMENTS

| | | | | |
|---|---|---|---|---|
| 4,658,365 A | * | 4/1987 | Syrett et al. ................ 205/724 |
| 4,695,385 A | * | 9/1987 | Boag ........................... 134/18 |
| 5,073,488 A | * | 12/1991 | Matner et al. ................. 435/31 |
| 5,213,760 A | * | 5/1993 | Dziabo et al. ............... 116/201 |
| 5,252,484 A | * | 10/1993 | Matner et al. ................. 422/55 |
| 5,366,872 A | * | 11/1994 | Hird et al. .................... 422/31 |
| 5,374,394 A | * | 12/1994 | Kralovic ...................... 422/28 |
| 5,518,927 A | * | 5/1996 | Malchesky et al. ........... 422/28 |
| 5,620,656 A | * | 4/1997 | Wensky et al. ............. 116/209 |
| 5,724,254 A | * | 3/1998 | Millett et al. ................ 702/179 |
| 5,757,666 A | * | 5/1998 | Schreiber et al. ........... 435/805 |
| 5,861,228 A | * | 1/1999 | Descales et al. .............. 422/62 |
| 5,900,256 A | * | 5/1999 | Scoville et al. ......... 252/186.29 |
| 5,906,802 A | * | 5/1999 | Langford .................... 134/170 |
| 5,928,948 A | * | 7/1999 | Malchesky ............. 250/339.11 |
| 6,096,270 A | * | 8/2000 | Rapkin et al. ................ 422/61 |
| 6,277,647 B1 | * | 8/2001 | CVhristner et al. ......... 436/165 |

* cited by examiner

Primary Examiner—Robert J. Warden, Sr.
Assistant Examiner—Sean E. Conley
(74) Attorney, Agent, or Firm—Wood, Herron & Evans, LLP

(57) ABSTRACT

A method to determine a reuse period for a high-level disinfectant without the need to perform a chemical test on the disinfectant during the reuse period. An algorithm for achieving a reuse period during which retesting is not required and based upon desired user stringency is disclosed. A computer program may be used to perform the algorithm. During the reuse period, the disinfectant is maintained in excess of the minimal effective concentration and may be reused on the same device after initial use or on a plurality of used devices. The method provides advantages in terms of cost and time efficiency since it eliminates the need to separately test the composition, and decreases variables associated with repeated testing of the disinfectant.

46 Claims, 2 Drawing Sheets

REUSE DETERMINATION FOR HIGH LEVEL DISINFECTANT

This application claims the benefit of U.S. Application Serial No. 60/235,727, filed Sep. 27, 2000.

FIELD OF THE INVENTION

The invention is directed to methods of determining a reuse period for a chemical disinfectant composition and methods of reusing a high level disinfectant without retesting efficacy of the active ingredient.

BACKGROUND

Instruments that are used in diagnostic or therapeutic procedures, which encompass surgical, medical, dental, etc. procedures, require decontamination to remove microbial contamination. Depending upon the ultimate use of the instrument, different degrees of decontamination are required.

As used herein, decontamination is the removal of hazardous or unwanted materials such as bacteria, mold spores or other pathogenic life forms and the like, wherein high-level disinfection and sterilization represent different levels of decontamination. Sterilization is a level of decontamination representing the complete elimination or destruction of all forms of microbial life, including fungal and bacterial spores. High-level disinfection is a level of decontamination representing elimination of many or all pathogenic microorganisms, with the exception of bacterial spores, from inanimate objects.

Regulatory agencies and other groups have classified medical devices, processes, and cleaning and decontaminating products according to basic principles related to infection control. Medical devices are classified as critical, semi-critical or noncritical. Critical devices, for example, scalpels, needles and other surgical instruments, enter sterile tissues or the vascular system. Such devices require sterilization with a process or with prolonged contact with a sporicidal chemical prior to reuse. A common way to sterilize critical devices is by exposure to heat. However, some instruments such as flexible lensed endoscopy instruments, inhalation therapy equipment, and other instruments and materials cannot withstand heat and must be treated with chemical solutions to achieve disinfection or sterilization. Such chemical solutions have included aldehydes, such as glutaraldehyde or o-phthaldehyde, or peracids.

Semicritical devices, for example, flexible endoscopes, bronchoscopes, laryngoscopes, endotracheal tubes and other similar instruments, are those that may contact any mucous membranes except dental mucous membranes. Such devices require high-level disinfection with a process or short contact with a sporicidal chemical prior to reuse. High-level disinfection can be expected to destroy all microorganisms with the exception of high numbers of bacterial spores. A Food and Drug Administration (FDA) regulatory requirement for high-level disinfectants is 100% kill of 100,000 to 1,000,000 ($10^5$–$10^6$) organisms of *Mycobacterium tuberculosis* (*M. tuberculosis*) in the presence of 2% horse serum in a quantitative tuberculocidal test. An additional FDA regulatory requirement for high-level disinfectants is that they must also achieve sterilization over a longer exposure time than the disinfection regimen time. Common high-level disinfectants include glutaraldehyde solutions between 2.4–3.4%$^{w/v}$ which also typically require activation with an alkaline buffer just prior to use, acidic hydrogen peroxide ($H_2O_2$) at 7.5%$^{w/v}$ (for example, Sporox®, Reckitt and Colman, Inc.), and an acidic mixture of 1.0%$^{w/v}$ $H_2O_2$ and 0.08%$^{w/v}$ peracetic acid (PAA) (Peract™ 20, Minntech Corp. or Cidex PA®, Johnson & Johnson). The minimum effective PAA concentration for high-level disinfection at 25 minutes (min) and 20° C. is 0.05%$^{w/v}$ (500 ppm) (Peract™ 20). The minimum effective $H_2O_2$ concentration for high-level disinfection at 30 min and 20° C. is 6.0%$^{w/v}$ (Sporox®).

High-level disinfecting solutions are typically designed for a reuse option, depending upon the type of device treated with the solution. The FDA currently approves the period during which a high level disinfectant may be reused. For example, the FDA has authorized a glutaraldehyde high-level disinfecting solution for endoscope reprocessing to be reused for as long as 28–30 days. The principle reason for reusing a solution is economic, as the practice itself provides the opportunity for adding to the risk of transmission of infection. The practice of reusing a high level disinfectant solution often results in a slow, continuous dilution of the solution over time, due to the inadvertent carry-over of rinse water into the disinfection solution. This rinse water may be present due to precleaning and rinsing prior to disinfection.

Medical devices such as thermometers and hydrotherapy tanks are also classified as semicritical, but they require intermediate-level rather than high-level disinfection prior to reuse. Intermediate-level disinfection inactivates *M. tuberculosis,* vegetative bacteria, most viruses and most fungi, but does not necessarily kill bacterial spores. A common intermediate-level disinfectant is Cavicide® (Metrex Research Corp.), which contains 0.28%$^{w/v}$ diisobutylphenoxyethoxyethyl dimethyl benzyl ammonium chloride, (a so-called super quat) and 17.2%$^{w/v}$ isopropyl alcohol.

Noncritical medical devices, for example, stethoscopes, tabletops, bedpans, etc., touch intact skin and require low-level disinfection prior to reuse. Low-level disinfection can kill most bacteria, some viruses, and some fungi, but it cannot be relied upon to kill resistant microorganisms such as tubercle bacilli or bacterial spores. Contact lenses are included in the class of devices which require low-level disinfection prior to reuse. Common low-level disinfectants for contact lens disinfection include acidic 3.0%$^{w/v}$ $H_2O_2$ and 1–10 ppm solutions of polymeric antimicrobial biguanides or quaternary ammonium compounds (e.g., 1 ppm polyhexamethylene biguanide in Complete® (Allergan Pharmaceuticals, Inc.) or 10 ppm Polyquad™ polyquaternary ammonium compound in Optifree® (Alcon, Inc.).

Standards for sterilization and low, intermediate and high-level disinfection have been concurrently established. These standards are based upon the known or possible risk of contamination of a particular medical device by a particular microorganism, the pathogenic nature of the organism and other principles in infection control. They typically require demonstration of sterilization and/or disinfection efficacy against a particular panel of test organisms, which collectively represent the known or possible contamination and infection risks. The test panels and criteria are different for low, intermediate or high-level disinfection. It is also generally accepted that a high-level disinfectant will meet the disinfection efficacy standards of intermediate and low-level disinfection as well. It is universally accepted that low-level disinfection performance cannot predict intermediate or high-level disinfection performance. In fact, it is assumed prior to testing that a low-level disinfectant cannot achieve a higher level disinfection standard. Additionally, other factors such as device compatibility with the disinfection system must also be considered. The current medical device industry practices for semicritical medical devices (i.e., those that contact intact skin and all but dental mucous membranes) such as endoscopes involve separate short cleaning and disinfecting steps and times, and reusable solutions. Longer soak cleaning or disinfecting times and single-use solutions would for the most part be impractical and uneconomical in the current environment.

Currently, the only way to be assured that a high level chemical disinfectant is, in fact, achieving high level disinfection is by daily monitoring of the disinfectant solution. For example, the solution may be monitored by using a test strip that is impregnated with or otherwise contains chemicals reactive with one or more active components of the solution. Generally, a color reaction occurs in the presence of a threshold concentration of a chemical decontaminant, which indicates to the user that the chemical is at a concentration sufficient to achieve its stated level of decontamination. This concentration is frequently reported as the minimum effective concentration (MEC). The results are generally qualitatively indicated to the user as either "pass" or "fail" as the user interprets the color change on the strip.

The use of chemical test strips to monitor the effectiveness of a decontaminant composition has inherent problems. One problem is that it adds another step to the process, adding cost, time, and another variable in which errors may occur. It also may not provide an accurate assessment of the composition efficacy. For example, a chemical test strip is used to monitor effectiveness of an acidic hydrogen peroxide ($H_2O_2$) solution at a concentration of $6.0\%^{w/v}$ or greater (Sporox I® and Sporox II®, Reckitt and Colman, Inc.). The reaction indicating effectiveness is based on the oxidation of iodide to iodine by the peroxide present in the composition. The strip contains iodide, horseradish peroxidase as the enzyme, and tetramethylbenzidine as the substrate. A blue color is produced on the strip in the presence of hydrogen peroxide at a concentration as low as 6.0%. However, the use of hydrogen peroxide alone at a concentration of up to 7.5% does not kill *M. tuberculosis*. Sporox I® and Sporox II® contain other excipients believed to be peracids, which are responsible for the tuberculocidal activity of the solutions. In fact, the manufacturer states that the test strip does not confirm disinfection or sterilization, and only indicates concentrations of hydrogen peroxide. The manufacturer also states that the test strip will give a "pass" result with any substance which will oxidize iodide to iodine and which is of sufficient strength. These substances include, among others, hypochlorite (bleach) and peracetic acid. Thus, this test strip is not specific for the active tuberculocidal component present in this disinfectant, nor does this test strip indicate the concentration of this component in the disinfectant.

In a disinfectant composition containing an acidic mixture of $1.0\%^{w/v}$ $H_2O_2$ and $0.08\%^{w/v}$ peracetic acid (PAA) (Peract[198] 20, Minntech Corp. or Cidex PA®, Johnson & Johnson), a test strip is used to monitor the MEC. However, this test strip yields a positive result even in the absence of the peracetic acid component, and will indicate efficacy even if only the hydrogen peroxide component of the composition is present. Thus, even though the composition utilizes both hydrogen peroxide and peracetic acid to achieve effective decontamination, the user of the test strip will be erroneously assured that the composition is effective even if its peracetic acid component is below its effective concentration or is missing altogether. As an additional troublesome factor, it is the peracetic acid component that is the principle tuberculocidal entity in the composition.

The effectiveness of an o-phthaldehyde-containing composition (Cidex® OPA, Johnson & Johnson) is also monitored using a test strip. This test strip will yield a positive result in the presence of any aldehyde, and therefore is not specific for the active o-phthaldehyde component. The manufacturer specifically states that the test strips cannot be used to validate the sterilization or disinfection process. So as before, the user may be mistakenly assured of the efficacy of the composition when, in fact, the composition is below the MEC due to a missing, altered, or inactive component.

It would thus be desirable to provide a non-chemical method for determining the reuse period for a high level disinfectant solution. The method would eliminate the use of test strips to monitor efficacy of the solution, with their attendant problems of additional procedures, costs, and potential sources of error. The method would also eliminate the problems of inaccurate results from the chemical test strip reactions. This invention is directed to such a method.

SUMMARY OF THE INVENTION

The invention is directed to a method of determining a period during which a high level disinfectant composition for a medical device may be reused without retesting the composition to determine efficacy of the active ingredient, and methods of reusing the composition without retesting.

In one embodiment of the method, the period is determined directly using an algorithm where the established or determined time period for reuse with testing, and during which the active ingredient remains at least at a minimum effective concentration (MEC) for high level disinfection, is reduced by a factor to determine a reuse period without the need for testing by dividing the established or determined time period by the factor. The factor is in the range of about 1.1 to 10.0. A factor of 1.1 provides a time period during which the active ingredient is present at about a 10% excess of the MEC. A factor of 10.0 provides about a 90% excess of the MEC. In another embodiment the factor is in the range of 1.25 and 5.

In another embodiment of the method, the period is determined indirectly using an algorithm where the difference in concentration between that used successfully at 100% of the labeled concentration of active ingredient and the minimum effective concentration is reduced by dividing by a factor to determine a reuse period without the need for testing. The reuse period here equals the time required for the active ingredient in the solution to reach this new lowest concentration based upon the new smaller differences in concentration from the 100% labeled concentrations. The factor is in the range of 1.1 to 10.0.

The method may be used to disinfect the same device reused over the period, or different devices. The time may be established by a regulatory agency or may be established by testing.

The invention is also directed to a method of reusing a high level disinfectant, containing an active ingredient that is present in at least a minimum effective concentration, without retesting efficacy of the active ingredient. In the method, the time for reusing the disinfectant is limited to a time that is not more than about 90% of the time, or a concentration that achieves a time that is not more than about 90% of the time in which the active ingredient remains at least at the MEC.

The invention is also directed to a method to high-level disinfect a device with a reused high level disinfectant having at least one active ingredient over a time period without retesting to determine efficacy of the active ingredient over the time period. The maximum time period for reusing the disinfectant with testing is divided by a factor to determine the reduced time period for reusing the disinfectant without testing. In one embodiment, the factor is between 1.1 and 10.0. In another embodiment the factor is between 1.25 and 5.

Alternatively, the period is determined by dividing the difference in concentration between that used and the MEC by a number between 1.1 and 10.0 to determine the lowest concentration for reusing the disinfectant without testing, and then determining the time for the active ingredient in the composition to reach this concentration. The high level disinfectant is reused without retesting over this time period to achieve high level disinfection of the device. Many devices, for example, medical devices that have been reused on either the same or different patients may be disinfected over this time period.

The invention is also directed to a method of achieving high level disinfection of at least one medical instrument by reusing a high level disinfection composition containing an active ingredient in at least a minimal effective concentration without performing a test on the composition during the reuse period to determine efficacy of the active ingredient. A period of time during which the active ingredient remains above a MEC for high level disinfection is obtained, and that time is divided by a number between 1.1 and 10.0 to determine a reuse period for the composition.

Alternatively, the period is determined by dividing the difference in concentration between that used and the MEC by a number between 1.1 and 10.0 to determine the lowest concentration for reusing the disinfectant without testing, and then determining the time for the active ingredient in the composition to reach this concentration. The instrument is exposed to the composition without retesting for efficacy of the active ingredient during this reuse period at a time and temperature sufficient to achieve high level disinfection.

For any of these methods, the calculations may be performed manually, or a computer program may perform part or all of the algorithm for a particular device, protocol, organism, and/or composition.

The invention will be further appreciated in light of the following figures, detailed description, and examples.

DETAILED DESCRIPTION

Figure 1:
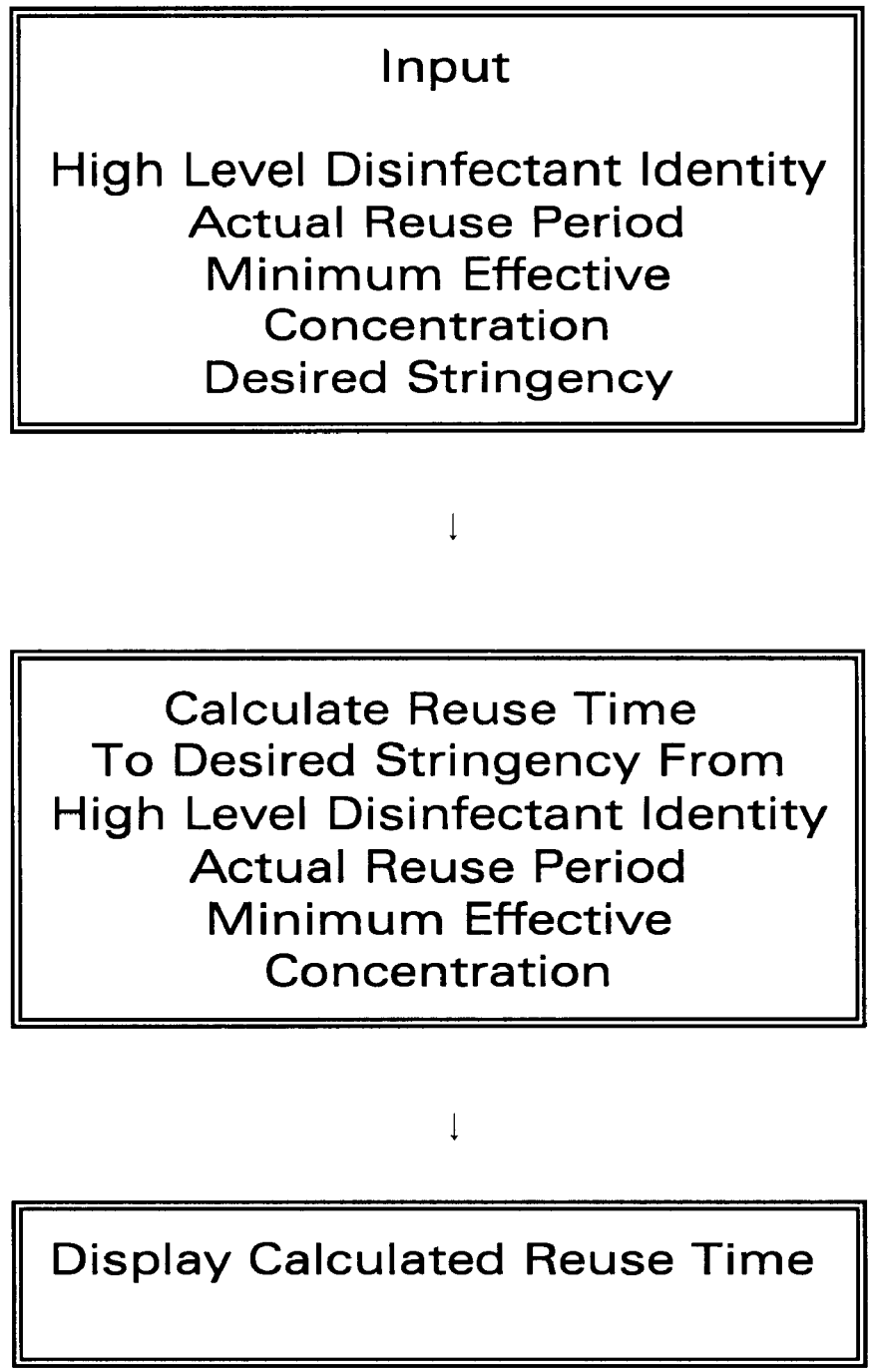
FIG. 1 is a flow chart for the inventive algorithm.

An actual reuse period for a chemical disinfectant solution is defined as the period during which the active component or components exists at its minimum effective concentration (MEC) at a specific temperature. The actual reuse period may be established by performing disinfection efficacy tests over a time period to determine the maximum time during which the solution maintains at least the MEC. Alternatively, the actual reuse period may be pre-established by a regulatory agency. A regulatory authorized reuse period is determined, for example, by a review of the information filed at the regulatory agency, which supports information provided on the label of the composition, in the package insert, or in the FDA 510(k) summary. The solution may achieve disinfection using oxidative chemicals such as peracetic acid, hydrogen peroxide, other peracids, and/or organic peroxides. Alternatively, the solution may achieve disinfection using non-oxidative chemicals such as aldehydes (e.g., o-phthaldehyde (OPA), and/or glutaraldehyde).

Using the inventive method, a reuse period during which the MEC is exceeded by a specified concentration for a particular disinfectant is calculated. The user is not required to retest the composition to verify that the active component or components are present in at least the MEC, and hence that the composition is effective for high level disinfection, throughout this reuse period.

In one embodiment of the method, the period is determined directly using an algorithm where the established or determined time period during which the active ingredient remains above a minimum effective concentration (MEC) for high level disinfection, is reduced by a factor to determine a reuse period without the need for testing that still provides the active ingredient(s) in at least approximately a 10% excess over the MEC.

In another embodiment of the method, the period is determined indirectly using an algorithm where the difference in concentration between that used successfully, preferably at 100% of the label concentration of the active ingredient, and the MEC is reduced by a factor to determine a reuse period without the need for testing. Due to the inverse relationship between concentration of active ingredient in the composition and reuse time, due to factors such as rinse water carry-over and dilution, as well as degradation of the active ingredient(s), it will be appreciated that the reuse period may be determined directly as a function of time, or indirectly as a function of a concentration that correlates to a particular time. This correlation may be performed using proportional relationships or graphical data and may be calculated manually or with the assistance of a computer software program.

The calculated reuse period for use without a test strip should assure a concentration of active disinfectant(s) at least about 10% in excess of the MEC during worse-case re-use conditions (e.g., maximum organic soil, rinse water carry-over, etc.), preferably 15% in excess of the MEC, and more preferably 20% in excess of the MEC, depending upon the degree of stringency desired. These guidelines for excess concentration are used to determine the reduction factor for a reuse period without retesting, and apply to both the direct embodiment and the indirect embodiment of the inventive method.

The invention determines the reuse period without the need to perform a daily chemical analysis, such as monitoring the disinfectant solution with a test strip based upon pre-established data. The invention provides a method for the user to reuse the composition in a time frame that is narrower than that provided by the established reuse period, but without the additional monitoring step and while still being assured of the efficacy of the composition. The invention provides a factor, based upon the established reuse period during which monitoring is required, to allow the user to determine the degree of stringency of the inventive system. The method permits the user to select the factor that will yield a more conservative or less conservative reuse time period, depending upon the particular circumstances, but always within a period during which efficacy is achieved. For example, the user may select a more conservative factor if the device is to be used on patients highly susceptible to infection, for example, immunocompromised patients. An ideal robust reuse period occurs when there is a maximum percentage difference between the label concentration of the active ingredient(s) and the MEC and between the use concentration of the active ingredients and the MEC. This maximizes the acceptable use dilution percent (e.g., use-dilution of the disinfectant solution from inadvertent carry-over of rinse water into the disinfectant solution) and allowed percent degradation of active ingredient(s), since monitoring of the efficacy of the test solution using test strips is not used at all times.

The inventive system has several advantages. The disinfection process is more cost-effective due to elimination of the need for at least daily or even more frequent testing of the composition during each disinfection cycle. If a test strip is used to test for efficacy, the test strips must be ordered, stocked, maintained, and used and interpreted correctly in order to achieve accurate results. If a test strip is not used, more complex chemical tests are needed to monitor efficacy of the active ingredient. Thus, the method decreases susceptibility to human error, and also allows the user to more easily stock, order, and determine future inventories for the composition. Furthermore, user liability is decreased because the method utilizes an inherent property of the solution which is used in establishing the authorized or determined reuse period, namely, the MEC of the active ingredient(s), then provides a further safety margin to ensure that effective disinfection is achieved and maintained throughout the reuse period without the need for additional testing.

One example in applying the inventive reuse period is determined from data provided in U.S. Pat. No. 5,900,256, assigned to Cottrell Ltd. and expressly incorporated by reference herein in its entirety. The '256 patent discloses that a composition containing hydrogen peroxide, peracetic acid, a corrosion inhibitor system, a surfactant and a stabilizer may be used to disinfect and sterilize medical instruments. The '256 patent is directed to a liquid chemical germicide in general, and to Endo-Spor Plus/Hyprocide® in particular, containing hydrogen peroxide and peracetic acid as the active components. The composition was classified under the Food and Drug Administration (FDA) guidelines as a sterilant for medical devices and was granted 510(k) approval. The 510(k) summary states that the sterilant is intended for the disinfection and sterilization of endoscopic instruments and other heat labile medical and dental instruments.

The '256 patent also discloses that the composition may be reused under heavy organic loads for a time period that is in excess of six weeks (greater than 42 days). The inventors determined this reuse period by measuring the percent by weight of hydrogen peroxide and peracetic acid in a 0.6:1 dilution of the composition at 0 and 45 days, and by measuring the percent by weight of hydrogen peroxide in a 0.4:1 dilution of the composition at 0 and 45 days. Application data submitted for regulatory approval confirmed stability of the composition to 46 days using a myriad of protocols (AOAC Sporicidal test using *Bacillus subtilis* and *Clostridium sporogenes*, a Simulated Use Test using *Mycobacterium bovis* and *Clostridium sporogenes*, a Quantitative Tuberculocidal Test using *Mycobacterium bovis*, an AOAC Use Dilution Test using *Pseudomonas aeruginosa, Staphylococcus aureus*, and *Salmonella choleraesius*, an EPA Virucidal test using Herpes simplex I, Poliovirus Type II, and Human Immunodeficiency Virus Type I, and an AOAC Fungicidal Test using *Trichophyton mentagrophytes*). Nonetheless, the FDA, in granting approval for this composition, stated that it may be used as a high level disinfectant with a contact time of 15 minutes at 20° C. under reuse conditions of up to 14 days.

Although the FDA 510(k) Summary lists details of Endo-Spor Plus in terms of Technological Characteristics and Performance Testing, it does not disclose how the allowed reuse period was determined. Moreover, chemical analysis of the germicide shows that it is effective in providing a MEC at a desired temperature for a period of time that is significantly longer than the FDA allowed reuse period, that is, 46 days versus up to 14 days.

Using the uppermost period for stability, 46 days, and dividing this by the regulatory permitted reuse period, 14 days, a factor of 3.29 is obtained. The inventive method, however, incorporates a wider range of 1.1 to 10.0 to provide a minimal built-in stringency to the system, while permitting the user to select the level of stringency desired. This factor provides the difference between an established reuse period and the reuse period actually obtainable without retesting, assuring the user that the high level disinfectant composition may be reused up to a calculated and finite time without any need to retest the solution throughout the entire period. Besides eliminating the need for daily chemical testing of the solution with its concomitant inconvenience, expense, and susceptibility to human error, the method provides the user assurance that the composition will be maintained at least at about 10% in excess of the MEC for the entire reuse period, due to the built-in stringency of the inventive method. This provides the additional benefits of minimizing user liability and human error.

In use, the label or package insert of a disinfectant solution requiring a reuse test provides a regulatory authorized established reuse period. Alternatively, an established reuse period may be determined from experimental data obtained from actual tests, as is known by one skilled in this art. The reuse period, typically given in days of reuse, is then further narrowed for calculating an actual reuse period without testing. This is accomplished by selecting a number between 1.1–10.0, by which the authorized reuse period is divided, to obtain the inventive period. If a more conservative reuse period is desired, the algorithm is set so that the authorized reuse period is divided by a number near or at the upper range. This may be desirable in several situations for example, when a new disinfectant composition is initiated by a user, when an institutional protocol requires a conservative reuse period, when it is convenient for personnel to change to a fresh solution at a particular time interval, when the instruments are to be used on a patient population particularly susceptible to infections so that increased stringency is warranted, etc. If a less conservative reuse period is desired, the algorithm is set so that a number near or at the lower limit of the range is divided by the authorized or measured reuse period. Even though selection of a number near the lower limit of the range provides a longer reuse period (that is, it provides a maximum reuse period that is closer to the established period), it still provides a period during which the active component or components will achieve at least about a 10% excess over the MEC throughout the entire period due to the built-in stringency of the system.

Alternatively, the factor may be expressed as a percentage of the period during which the solution is maintained at a defined excess over its MEC. Expressed as a percentage, the factor is usually between 10% and 90% of the period during which the composition has at least a MEC for a high level disinfectant. For example, to obtain a less stringent reuse period, the reuse period may be expressed as exceeding the MEC by about 10% by dividing the authorized reuse period by a factor of 1.1. To obtain a more stringent reuse period, the higher percentage by which the MEC is exceeded, for example, 15%, 20%, or even higher and up to about 90%, depending upon the stringency, is required. The lower number, which provides the upper reuse limit (that is, a factor of 1.1 by which an authorized reuse period is divided, which equates to about a 10% excess over the MEC) is set to provide the maximum reuse time while still achieving a desired degree of certainty. Any factor exceeding this can be used to provide an additional degree of certainty, which may be desired depending upon the particular circumstances, and on occasion may be about a 90% excess over the MEC.

The calculation may be accomplished in a number of ways. In one embodiment, a computer software program that is able to calculate the reuse time period range upon entry of the regulatory reuse period may be used. In this embodiment, a range of regulatory reuse periods may be entered for a number of compositions, with the user simply choosing the desired factor or stringency. FIG. 1 shows a flow chart for accomplishing the calculation. The regulatory authorized or experimentally calculated reuse period for the particular disinfectant composition is entered into the system. As previously stated, this will be available from the label or package insert, or from test data. For example, if an authorized reuse period has not been determined, it may be established by testing to generate the type of data required in submitting a 510(k) application to the FDA.

Figure 2:
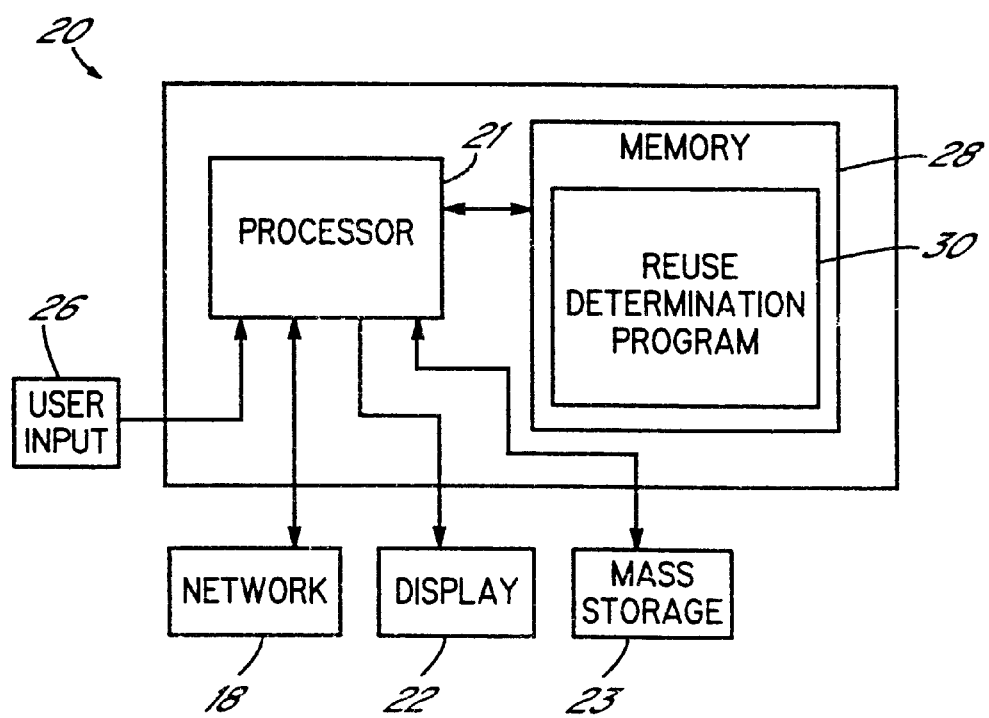
FIG. 2 is a block diagram of a computer system with an exemplary software environment for the computer system.

FIG. 2 shows an illustrative computer system 20 for performing this task. The computer system 20 may include a processor 21 such as a microprocessor, a number of peripheral components such as a computer display 22, storage device 23 such as hard, floppy, and/or CD-ROM disk drives, a printer (not shown), and various user input devices 26 (e.g., a mouse and keyboard), among others. Computer system 20 operates under the control of an operating system resident in a memory 28 and executes various computer software applications, programs, objects, modules, etc. Computer system 20 may also be coupled to other computers via a network 18. To perform reuse determination consistent with the invention, computer system 20 is typically under the control of a reuse determination program 30.

It should be appreciated that program may be stored on network 18 or mass storage 23 prior to start-up. In addition, it may have various components that are resident at different times in any of memory 28, mass storage 23, network 18, or within registers and/or caches in processor 21 (e.g., during execution thereof). It should also be appreciated that other software environments may be utilized in the alternative.

In another embodiment of the invention, a manual calculation may be used to perform the algorithm. In this embodiment, the regulatory reuse period for the desired composition, the MEC of the composition, the desired factor, and the computation directive is selected and executed to obtain a reuse period. The calculation may be performed with or without the assistance of a calculator.

The invention will be further appreciated in light of the following examples.

EXAMPLE 1

Cidex® (Johnson & Johnson) contains 2.4% by weight glutaraldehyde as the active ingredient. In a two step regimen with activation, instrument sterilization is achieved by contact for 10 h at 25° C., and high level disinfection is achieved by contact for 45 min at 25° C. The manufacturer recites a reuse period of 14 days with a separate test strip as a reuse indicator. Using the inventive method, the composition may be reused during a period of time ranging from at least 1 day (14 days/10.0=1.4) to at least 12 days (14 days/1.1=12.7) without the need for retesting with a separate test strip.

EXAMPLE 2

Cidex Formula 7® (Johnson & Johnson) contains 2.5% by weight glutaraldehyde as the active ingredient. In a two step regimen with activation, instrument sterilization is achieved by contact for 10 h at 20–25° C., and high level disinfection is achieved by contact for 90 min at 25° C. The manufacturer recites a reuse period of 28 days with a separate test strip as a reuse indicator. Using the inventive method, the composition may be reused during a period of time ranging from at least 2 days (28 days/10.0=2.8) to at least 25 days (28 days/1.1=25.4) without the need for retesting with a separate test strip.

EXAMPLE 3

Cidex Plus® (Johnson & Johnson) contains 3.4% by weight glutaraldehyde as the active ingredient. In a two step regimen with activation, instrument sterilization is achieved by contact for 10 h at 20–25° C., and high level disinfection is achieved by contact for 20 min at 25° C. The manufacturer recites a reuse period of 28 days with a separate test strip as a reuse indicator. Using the inventive method, the composition may be reused during a period of time ranging from at least 2 days (28 days/10.0=2.8) to at least 25 days (28 days/1.1=25.4) without the need for retesting with a separate test strip.

EXAMPLE 4

Metricide 14® (Metrex Research) contains 2.6% by weight glutaraldehyde as the active ingredient. In a two step regimen with activation, instrument sterilization is achieved by contact for 10 h at 25° C., and high level disinfection is achieved by contact for 45 min at 25° C. The manufacturer recites a reuse period of 14 days with a separate test strip as a reuse indicator. Using the inventive method, the composition may be reused during a period of time ranging from at least 1 day (14 days/10.0=1.4) to at least 12 days (14 days/1.1=12.7) without the need for retesting with a separate test strip.

EXAMPLE 5

Metricide Plus 30® (Metrex Research) contains 3.4% by weight glutaraldehyde as the active ingredient. In a two step regimen with activation, instrument sterilization is achieved by contact for 10 h at 25° C., and high level disinfection is achieved by contact for 90 min at 25° C. The manufacturer recites a reuse period of 28 days with a separate test strip as a reuse indicator. Using the inventive method, the composition may be reused during a period of time ranging from at least 2 days (28 days/10.0=2.8) to at least 25 days (28 days/1.1=25.4) without the need for retesting with a separate test strip.

EXAMPLE 6

Metricide 28 Day® (Metrex Research) contains 2.5% by weight glutaraldehyde as the active ingredient. In a two step regimen with activation, instrument sterilization is achieved by contact for 10 h at 25° C., and high level disinfection is achieved by contact for 90 min at 25° C. The manufacturer recites a reuse period of 28 days with a separate test strip as a reuse indicator. Using the inventive method, the composition may be reused during a period of time ranging from at least 2 days (28 days/10.0=2.8) to at least 25 days (28 days/1.1=25.4) without the need for retesting with a separate test strip.

EXAMPLE 7

Procide 14 N.S.® (Cottrell Limited) contains 2.4% by weight glutaraldehyde as the active ingredient. In a two step regimen with activation, instrument sterilization is achieved by contact for 10 h at 20° C., and high level disinfection is achieved by contact for 45 min at 20° C. The manufacturer recites a reuse period of 14 days with a separate test strip as a reuse indicator. Using the inventive method, the composition may be reused during a period of time ranging from at least 1 day (14 days/10.0=1.4) to at least 12 days (14 days/1.1=12.7) without the need for retesting with a separate test strip.

EXAMPLE 8

Omnicide Long Lf® (Cottrell Limited) contains 2.4% by weight glutaraldehyde as the active ingredient. In a two step regimen with activation, instrument sterilization is achieved by contact for 10 h at 20° C., and high level disinfection is achieved by contact for 45 min at 20° C. The manufacturer recites a reuse period of 28 days with a separate test strip as a reuse indicator. Using the inventive method, the composition may be reused during a period of time ranging from at least 2 days (28 days/10.0=2.8) to at least 25 days (28 days/1.1=25.4) without the need for retesting with a separate test strip.

EXAMPLE 9

Omnicide Plus® (Cottrell Limited) contains 3.4% by weight glutaraldehyde as the active ingredient. In a two step regimen with activation, instrument sterilization is achieved by contact for 10 h at 20° C., and high level disinfection is achieved by contact for 45 min at 20° C. The manufacturer recites a reuse period of 28 days with a separate test strip as a reuse indicator. Using the inventive method, the composition may be reused during a period of time ranging from at least 2 days (28 days/10.0=2.8) to at least 25 days (28 days/1.1=25.4) without the need for retesting with a separate test strip.

EXAMPLE 10

Wavicide-01® (Wave Energy Systems) contains 2.5% by weight glutaraldehyde as the active ingredient. In a two step regimen with activation, instrument sterilization is achieved by contact for 10 h at 22° C., and high level disinfection is achieved by contact for 45 min at 22° C. The manufacturer recites a reuse period of 30 days with a separate test strip as a reuse indicator. Using the inventive method, the composition may be reused during a period of time ranging from at least 3 days (30 days/10.0=3) to at least 27 days (30 days/1.1=27.3) without the need for retesting with a separate test strip.

EXAMPLE 11

Peract 20® (Minntech Corporation) contains 0.08% by weight peracetic acid and 1% by weight hydrogen peroxide as the active ingredients. In a one step regimen, instrument sterilization is achieved by contact for 8 h at 20° C., and high level disinfection is achieved by contact for 25 min at 20° C. The manufacturer recites a reuse period of 14 days with a separate test strip as a reuse indicator. Using the inventive method, the composition may be reused during a period of time ranging from at least 1 day (14 days/10.0=1.4) to at least 12 days (14 days/1.1=12.7) without the need for retesting with a separate test strip.

EXAMPLE 12

Sporox® (Steris Corporation) contains 7.5% by weight $H_2O_2$ as the stated active ingredient. Sterilization is achieved by contact for 6 h at 20° C. High level disinfection is achieved by contact for 30 min. The reuse period is 21 days. Using the inventive method, the composition may be reused during a period of time ranging from at least 2 days (21/10.0=2.1) to at least 19 days (21/1.1=19.1) without the need for retesting with a separate test strip.

EXAMPLE 13

Cidex® OPA (Johnson & Johnson) contains 0.55% of o-phthalaldehyde as the active ingredient. Instrument sterilization is achieved by contact for 10 h at 25° C. or 32 h at 20° C. The manufacturer states that the MEC is 0.30%, there is a single use sterilization, and that a reuse period for high level disinfection is 14 days. The percentage decrease between the concentration stated on the label and the MEC is 45.5% ((0.55%–0.30%)/0.55%). Using the inventive method, the composition may be reused during a period of time ranging from at least 1 day (14 days/10.0=1.4) to at least 12 days (14 days/1.1=12.7) without the need for retesting with a separate test strip.

Alternatively, the percentage decrease of 45.5% may be divided by a number between 1.1 and 10, and then the amount of time for the concentration to reach approximately a 10–90% excess over the MEC may be determined. For example, 45.5%/1.1=41.4%. In the calculation ((0.55%–x)/0.55%) (100)=41.4%, x=0.32%. The new reuse period is the amount of time required to reach 0.32%, about 7% (relative) over the MEC.

EXAMPLE 14

Cidex PA® (Johnson & Johnson) contains 0.08% by weight peracetic acid as the active ingredient and 1.0% by weight $H_2O_2$. The sterilization time is 8 h at 20° C. The manufacturer states that the MEC is 0.05% peracetic acid and that a reuse period is 14 days. The percentage decrease between the concentration stated on the label and the MEC is 37.5% ((0.08%–0.05%)/0.08%). Using the inventive method, the composition may be reused during a period of time ranging from at least 1 day (14 days/10.0=1.4) to at least 12 days (14 days/1.1=12.7) without the need for retesting with a separate test strip.

Alternatively, the percentage decrease of 37.5% may be divided by a number between 1.1 and 10, and then the amount of time for the concentration to reach a 10–90% excess over the MEC may be determined.

EXAMPLE 15

Sporox® contains 7.5% by weight $H_2O_2$ as the active ingredient. The manufacturer states that its MEC is 6.0% by weight and that a reuse period is 21 days. The percentage decrease between the concentration stated on the label and the MEC is 20% ((7.5%–6.0%)/7.5%). Using the inventive method, the composition may be reused during a period of time ranging from at least 2 days (21 days/10.0=2.1) to at least 19 days (21 days/1.1=19) without the need for retesting with a separate test strip.

Alternatively, the percentage decrease of 20% may be divided by a number between 1.1 and 10, and then the amount of time for the concentration to reach a 10–90% excess over the MEC may be determined.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A method of determining a period during which a high level disinfectant composition for a medical device comprising at least one active ingredient may be reused without retesting the composition to determine efficacy of the active ingredient comprising
   a. determining a period of time in which the active ingredient remains at least at a minimum effective concentration for said high level disinfection, and
   b. dividing that period of time by a factor between 1.1 and 10.0 to determine said reuse period without retesting.

2. The method of claim 1 wherein the factor is between 1.25 and 5.0.

3. The method of claim 1 wherein step (a) is performed using a regulatory authorized period.

4. The method of claim 1 wherein step (a) is performed using experimental data.

5. The method of claim 1 performed by a computer.

6. A method of determining a period during which a high level disinfectant composition for a medical device comprising at least one active ingredient may be reused without retesting the composition to determine efficacy of the active ingredient and reusing the composition for high level disinfection, the method comprising
   a. determining a period of time in which the active ingredient remains at least at a minimum effective concentration for said high level disinfection,
   b. dividing said period of time by a factor between 1.1 and 10.0 to determine said reuse period without retesting, and
   c. reusing said composition during said period in (b).

7. The method of claim 6 wherein said composition is reused to achieve a minimal effective concentration (MEC) of said composition at a specified temperature.

8. The method of claim 6 wherein the high level disinfectant is selected from the group consisting of an oxidative disinfectant and a non-oxidative disinfectant.

9. The method of claim 6 wherein the factor is between 1.25 and 5.0.

10. A method of reusing a high level disinfectant containing an active ingredient present in at least a minimum effective concentration (MEC) without retesting efficacy of the active ingredient during reuse comprising
    establishing a time period for reusing the disinfectant at which the active ingredient remains at least about 10% above the MEC, and
    reusing the disinfectant without retesting for the established time period to achieve high level disinfection during the established time period.

11. The method of claim 10 wherein said time is that at which the active ingredient remains in the range of about 10%–90% above the MEC.

12. The method of claim 10 wherein said time is that at which the active ingredient remains in the range of about 10%–50% above the MEC.

13. The method of claim 10 wherein said time is established using a specially programed computer.

14. A method to high-level disinfect a plurality of devices requiring high level disinfecting with a reused high level disinfectant having at least one active ingredient over a time period without testing over the time period to determine efficacy of the active ingredient comprising
    (a) dividing a maximum time period for reusing the disinfectant with testing by a factor between 1.1 and 10.0 to determine the time period for reusing the disinfectant without testing, and
    (b) reusing the high level disinfectant to high level disinfect a plurality of devices requiring high level disinfection without testing to achieve high level disinfection of the device during the time period for reusing in (a).

15. The method of claim 14 wherein the factor is between 1.25 and 5.0.

16. The method of claim 14 wherein the devices are medical devices.

17. A method of achieving high level disinfection for at least one medical instrument by reusing a high level disinfection composition containing an active ingredient in at least a minimal effective concentration (MEC) during a period of time without retesting said composition to determine efficacy of the active ingredient comprising
    a. determining a period of time during which the active ingredient remains at least at a MEC for high level disinfection,
    b. dividing the period of time in (a) by a factor between 1.1 and 10.0 to determine a reuse period for the composition, and
    c. exposing the instrument to the composition at any point throughout the period of time in (b) at a temperature and duration sufficient to achieve high level disinfection.

18. The method of claim 17 wherein the factor in (b) is between 1.25 and 5.0.

19. The method of claim 17 wherein the factor in (b) is selected to provide a desired stringency of said method.

20. The method of claim 17 performed by a specially programmed computer.

21. A method of determining a period during which a high level disinfectant composition may be reused without retesting the composition comprising the steps of
    a. determining a period during which the composition has at least a minimum effective concentration for said high level disinfection, and
    b. thereafter decreasing said period in (a) by a factor between about 10% and 90% to provide said reuse period without retesting.

22. The method of claim 21 wherein the factor is between about 10% and 50%.

23. A method of determining a period during which a high level disinfectant composition comprising at least one active ingredient may be reused on a medical device without retesting the composition to determine efficacy of the active ingredient comprising
    a. determining the difference in concentration between 100% of the labeled active ingredient in the composition and the minimum effective concentration (MEC) of the active ingredient,
    b. dividing the difference by a factor between 1.1 and 10.0 to determine a minimum concentration for reuse without retesting, and
    c. determining the period for reuse without testing by determining a time for the active ingredient to reach the concentration in (b).

24. The method of claim 23 wherein the factor is between 1.25 and 5.0.

25. The method of claim 23 wherein the concentrations in step (a) are determined from published information.

26. The method of claim 23 wherein the concentration of active ingredient is provided by the manufacturer.

27. The method of claim 23 wherein the time in step (c) is determined from information supplied by the manufacturer.

28. The method of claim 23 wherein the time in step (c) is determined experimentally.

29. The method of claim 23 performed by a specially programmed computer.

30. A method of determining a period during which a high level disinfectant composition for a medical device comprising at least one active ingredient may be reused without retesting the composition to determine efficacy of the active ingredient and reusing the composition, the method comprising
   a. determining the difference in concentration between 100% of the labeled active ingredient in the composition and the minimum effective concentration (MEC) of the active ingredient,
   b. dividing the difference by a factor between 1.1 and 10.0 to determine a minimum concentration for reuse without retesting,
   c. determining the period for reuse without testing by determining a time for the active ingredient to reach the concentration in (b), and
   d. reusing said composition during said period determined in (c).

31. The method of claim 30 wherein the factor is between 1.25 and 5.0.

32. The method of claim 30 wherein said composition is reused for the determined period to achieve high-level disinfection of a plurality of said devices during said period.

33. The method of claim 30 wherein said composition is reused for the determined period to achieve a concentration at least about 10% in excess of the MEC of said composition at a specified temperature.

34. The method of claim 30 wherein said composition is reused for the determined period to achieve a concentration in the range between 10% and 90% in excess of the MEC of said composition at a specified temperature.

35. The method of claim 30 wherein said composition is reused for the determined period to achieve a concentration in the range between 10% and 50% in excess of the MEC of said composition at a specified temperature.

36. The method of claim 30 wherein the high level disinfectant is selected from the group consisting of an oxidative disinfectant and a non-oxidative disinfectant.

37. A method of reusing a high level disinfectant containing an active ingredient present in excess of the minimum effective concentration (MEC) without retesting efficacy of the active ingredient during reuse comprising
   establishing a concentration for reusing the disinfectant to said concentration which achieves a reuse time that is not more than about 90% of a time to reach a concentration in which the active ingredient remains above the MEC, and
   reusing the disinfectant without retesting for the reuse time to achieve high level disinfection.

38. The method of claim 37 wherein said time is from 10% to 90% of the time to reach said concentration in which the active ingredient remains above the MEC.

39. The method of claim 37 wherein said time is from 10% to 50% of the time to reach said concentration in which the active ingredient remains above the MEC.

40. The method of claim 37 wherein said reuse concentration is determined by a specially programmed computer.

41. A method to high-level disinfect a plurality of devices requiring high level disinfecting with a reused high level disinfectant having at least one active ingredient over a time period without testing over the time period to determine efficacy of the active ingredient comprising
   a. determining the difference in concentration between the active ingredient in the composition and the minimum effective concentration (MEC) of the active ingredient,
   b. dividing the difference by a factor between 1.1 and 10.0 to determine a minimum concentration for reusing the disinfectant without retesting,
   c. determining the period for reuse without testing by determining a time for the active ingredient to reach the concentration in (b), and
   d. reusing the high level disinfectant to high level disinfect a plurality of devices requiring high level disinfection without testing to achieve high level disinfection of the device at any point throughout the time period determined in (c).

42. The method of claim 41 wherein the factor is between 1.25 and 5.0.

43. The method of claim 41 wherein the device is a medical device.

44. A method to achieve high level disinfection for at least one medical instrument requiring high level disinfecting with a reused high level disinfectant composition containing an active ingredient in excess of the minimal effective concentration (MEC) during a period of time without retesting said composition to determine efficacy of the active ingredient comprising
   a. determining the difference in concentration between the active ingredient in the composition and the MEC of the active ingredient,
   b. dividing the difference by a factor between 1.1 and 10.0 to determine a minimum concentration for reusing the disinfectant without retesting,
   c. determining the period for reuse without testing by determining a time for the active ingredient to reach the concentration in (b), and
   d. exposing the instrument to the composition at any point throughout the period of time in (c) at a temperature and duration sufficient to achieve high level disinfection.

45. The method of claim 44 wherein said number in (b) is selected to provide a desired stringency of said method.

46. The method of claim 44 wherein steps a, b, and/or c are performed by a specially programmed computer.

* * * * *

UNITED STATES PATENT AND TRADEMARK OFFICE
CERTIFICATE OF CORRECTION

PATENT NO. : 6,468,469 B2  
DATED : October 22, 2002  
INVENTOR(S) : Huth

It is certified that error appears in the above-identified patent and that said Letters Patent is hereby corrected as shown below:

<u>Column 3,</u>
Line 52, reads "Peract$^{198}$ 20," and should read -- Peract $^{TM}$ 20, --.

Signed and Sealed this

First Day of July, 2003

JAMES E. ROGAN
*Director of the United States Patent and Trademark Office*